(12) United States Patent
Pagé et al.

(10) Patent No.: US 7,244,850 B2
(45) Date of Patent: *Jul. 17, 2007

(54) BENZIMIDAZOLE DERIVATIVES, COMPOSITIONS CONTAINING THEM, PREPARATION THEREOF AND USES THEREOF

(75) Inventors: Daniel Pagé, St. Laurent (CA); Christopher Walpole, St. Laurent (CA); Hua Yang, St. Laurent (CA)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/559,887

(22) PCT Filed: Jun. 9, 2004

(86) PCT No.: PCT/GB2004/002429

§ 371 (c)(1),
(2), (4) Date: Dec. 7, 2005

(87) PCT Pub. No.: WO2004/108689

PCT Pub. Date: Dec. 16, 2004

(65) Prior Publication Data

US 2006/0142364 A1 Jun. 29, 2006

(30) Foreign Application Priority Data

Jun. 10, 2003 (SE) .................................. 0301698

(51) Int. Cl.
*A61K 31/4184* (2006.01)
*C07D 235/08* (2006.01)

(52) U.S. Cl. .................................. 548/304.4; 514/394

(58) Field of Classification Search ............. 548/304.4
See application file for complete search history.

(56) References Cited

U.S. PATENT DOCUMENTS 6,348,032 B1 2/2002 Sperl et al.

FOREIGN PATENT DOCUMENTS

| EP | 0882718 A | 12/1998 |
|---|---|---|
| WO | 02/085866 A | 10/2002 |
| WO | 03/027076 A | 4/2003 |
| WO | 03/053938 A | 7/2003 |
| WO | 2004/035548 A | 4/2004 |

OTHER PUBLICATIONS

CAPLUS accession No. 2000:214835, doc. No. 132:265201, Takeda Chemical Ind. Ltd., "Preparation of imidazole . . . hormone antagonists" JP,A2,2000095767. Apr. 4, 2000.
CAPLUS accesssion No. 1996:323082, doc. No. 125:10810, Kureha Chem. Ind. Co. Ltd. "Preparation and formulation . . . treatment of kidney diseases" JP,A2,08048671, Feb. 20, 1996.
CAPLUS accession No. 1996:110144, doc. No. 124:260950, Xue, C. et al., "Design synthesis . . . of benzimidazole . . . inhibitors," Bio & Med. Chem. Letters (1996), 6(3), pp. 339-344.
CAPLUS accession No. 1957:70445, doc No. 51:70445, General Aniline & Film Corporation.: "Pinakryptol Yellow," US 2794802, Jun. 4, 1957.
CAPLUS accession No. 2003:215662, doc. No. 139:133505, Vourloumis, D. et al., "Solid-phase synthesis of . . . biases for RNA targets," Tetrahedron Letters (2003), 44(14), pp. 2807-2811.
CAPLUS accession No. 1997:476314, doc. No. 127:135799, Yamasaki, N. et al., "Preparation of benzimidazole derivatives as drugs,", 1997.
CHEMCATS accession No. 2003:825404, "1H-Benzimidazole-5-carboxamide, 1-ethyl-N,2-dimethyl-," CAS Registry 313373-88-5, 2003.
Goker, H. et al., "Synthesis of some new benzimidazolecarboxamides and evaluation of their antimicrobial activity," Farmaco, Societa Chim Italiana, vol. 53, No. 6, 1998, pp. 415-420, XP-000942653, table 1.
Goker, H. et al., "Synthesis of 1,2-Disubstituted benzimidazole-5(6)-carboxamides and evaluation of their antimicrobial activity," Farmaco, Societa Chim Italiana, vol. 51, No. 1, 1996, pp. 53-58, XP-000942654, table 1.
Goker, H. et al., "Synthesis of some new 2-substituted-phenyl-1H-benzimidazole-5-carbonitriles and their potent activity against Candida Species," Bioorganic & Medicinal Chemistry, vol. 10, 2002, pp. 2589-2596, XP-002295583, examples 37, 39; table 1.
Patent Abstracts of Japan, vol. 0176, No. 74 (C-1140) Dec. 10, 1993 & JP 5222000 A (Fujisawa Pharmaceut Co. Ltd.), Aug. 31, 1993, RN 152712-72-6, abstract.
Patent Abstracts of Japan, vol. 1996, No. 06, Jun. 28, 1996 & JP 8048671 A (Kureha Chem Ind. Co. Ltd.), Feb. 20, 1996, RN 176963-84-1, abstract.
CHEMCATS accession No. 2005:1008576, "1H-Benzimidazole-5-carboxamide, 1-ethyl-N,N,2-trimethyl-," CAS Registry No. 313277-30-4, 2005.

(Continued)

Primary Examiner—Laura L. Stockton
(74) Attorney, Agent, or Firm—Jianzhong Shen

(57) ABSTRACT

Compounds of formula (I) or pharmaceutically acceptable salts thereof: Formula (I) wherein $R^1$, $R^2$, $RF^1$, $RF^2$ and Z are as defined in the specification as well as salts and pharmaceutical compositions including the compounds are prepared. They are useful in therapy, in particular in the management of pain

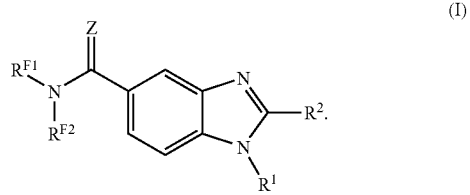

14 Claims, No Drawings

OTHER PUBLICATIONS

CHEMCATS accession No. 2004:3262685, "1H-Benzimidazole-5-carboxamide, 1-ethyl-N,N,2-trimethyl," CAS Registry No. 313277-30-4, 2004.

CHEMCATS accession No. 2004:1816507, "1H-Benzimidazole-5-carboxamide, 1-ethyl-N,N,2-trimethyl," CAS Registry No. 313277-30-4, 2004.

CHEMCATS accession No. 2004:1348130, "1-ethyl-N,N,2-trimethyl-1H-benzimidazole-5-carboxamide," CAS Registry No. 313277-30-4, 2004.

CHEMCATS accession No. 2003:2201477, "1H-Benzimidazole-5-carboxamide, 1-ethyl-N,N,2-trimethyl," CAS Registry No. 313277-30-4, 2003.

CHEMCATS accession No. 2003:2105385, "1H-Benzimidazole-5-carboxamide, 1-ethyl-N,N,2-trimethyl," CAS Registry No. 313277-30-4, 2003.

CHEMCATS accession No. 2001:2782293, "1H-Benzimidazole-5-carboxamide, 1-ethyl-N,N,2-trimethyl," CAS Registry No. 313277-30-4, 2001.

CHEMCATS accession No. 2001:960231, "1H-Benzimidazole-5-carboxamide, 1-ethyl-N,N,2-trimethyl," CAS Registry No. 313277-30-4, 2001.

CHEMCATS accession No. 2001:23886, "1H-Benzimidazole-5-carboxamide, 1-ethyl-N,N,2-trimethyl," CAS Registry No. 313277-30-4, 2001.

CHEMCATS accession No. 2005:3992456, "1H-Benzimidazole-5-carboxamide, 1-ethyl-N,2-dimethyl-" CAS Registry No. 313373-88-5, 2005.

CHEMCATS accession No. 2001:2782292, "1H-Benzimidazole-5-carboxamide, 1-ethyl-N,2-dimethyl-" CAS Registry No. 313373-88-5, 2001.

CHEMCATS accession No. 2001:2447450, "1H-Benzimidazole-5-carboxamide, 1-ethyl-N,2-dimethyl-" CAS Registry No. 313373-88-5, 2001.

CHEMCATS accession No. 2001:1569813, "1H-Benzimidazole-5-carboxamide, 1-ethyl-N,2-dimethyl-" CAS Registry No. 313373-88-5, 2001.

BENZIMIDAZOLE DERIVATIVES, COMPOSITIONS CONTAINING THEM, PREPARATION THEREOF AND USES THEREOF

CROSS-REFERENCE TO RELATED APPLICATIONS

This application is a US National Stage under 35 U.S.C § 371 of International Application No. PCT/GB2004/002429, filed on 9 Jun. 2004, which claims priority under 35 U.S.C. § 119(a)-(d) to Swedish Application No. 0301698-7 filed on 10 Jun. 2003.

BACKGROUND OF THE INVENTION

1. Field of the Invention

The invention is related to therapeutic compounds which are $CB_1$ receptor ligands, pharmaceutical compositions containing these compounds, manufacturing processes thereof and uses thereof, and more particularly to compounds that are $CB_1$ receptor agonists. More particularly, the present invention is related to compounds that may be effective in treating pain, cancer, multiple sclerosis, Parkinson's disease, Huntington's chorea, Alzheimer's disease, anxiety disorders, Gastrointestinal disorders and cardiavascular disorders.

2. Discussion of Relevant Technology

Pain management has been an important field of study for many years. It has been well known that cannabinoid receptor (e.g., $CB_1$ receptor, $CB_2$ receptor) ligands including agonists, antagonists and inverse agonists produce relief of pain in a variety of animal models by interacting with $CB_1$ and/or $CB_2$ receptors. Generally, $CB_1$ receptors are located predominately in the central nervous system, whereas $CB_2$ receptors are located primarily in the periphery and are primarily restricted to the cells and tissues derived from the immune system.

While $CB_1$ receptor agonists, such as $\Delta^9$-tetrahydrocannabinol ($\Delta^9$-THC) and anadamide, are useful in anti-nociception models in animals, they tend to exert undesired CNS side-effects, e.g., psychoactive side effects, the abuse potential, drug dependence and tolerance, etc. These undesired side effects are known to be mediated by the $CB_1$ receptors located in CNS. There are lines of evidence, however, suggesting that CB1 agonists acting at peripheral sites or with limited CNS exposure can manage pain in humans or animals with much improved overall in vivo profile.

Therefore, there is a need for new $CB_1$ receptor ligands such as agonists, antagonists or inverse agonists that are useful in managing pain or treating other related symptoms or diseases with reduced or minimal undesirable CNS side-effects.

DISCLOSURE OF THE INVENTION

The present invention provides $CB_1$ receptor ligands which are useful in treating pain and other related symptoms or diseases.

DEFINITIONS

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

"$CB_1$/$CB_2$ receptors" means $CB_1$ and/or $CB_2$ receptors.

The term "$C_{m-n}$" or "$C_{m-n}$ group" used alone or as a prefix, refers to any group having m to n carbon atoms, and having 0 to n multivalent heteroatoms selected from O, S, N and P, wherein m and n are 0 or positive integers, and n>m. For example, "$C_{1-6}$" would refer to a chemical group having 1 to 6 carbon atoms, and having 0 to 6 multivalent heteroatoms selected from O, S, N and P.

The term "hydrocarbon" used alone or as a suffix or prefix, refers to any structure comprising only carbon and hydrogen atoms up to 14 carbon atoms. The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to monovalent straight or branched chain hydrocarbon radicals comprising 1 to about 12 carbon atoms. Unless otherwise specified, "allyl" general includes both saturated allyl and unsaturated alkyl.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms.

The term "alkynyl" used alone or as suffix or prefix, refers to a monovalent straight or branched chain hydrocarbon radical having at least one carbon-carbon triple bond and comprising at least 2 up to about 12 carbon atoms.

The term "cycloalkyl," used alone or as suffix or prefix, refers to a monovalent ring-containing hydrocarbon radical comprising at least 3 up to about 12 carbon atoms.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms, wherein the radical is located on a carbon of the aromatic ring.

The term "non-aromatic group" or "non-aromatic" used alone, as suffix or as prefix, refers to a chemical group or radical that does not containing a ring having aromatic character (e.g., 4n+2 delocalized electrons).

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to links two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroalkyl" used alone or as a suffix or prefix, refers to a radical formed as a result of replacing one or more carbon atom of an alkyl with one or more heteroatoms selected from N, O, P and S.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen from a carbon of a ring of the heterocycle.

The term "heterocyclylene" used alone or as a suffix or prefix, refers to a divalent radical derived from a heterocycle by removing two hydrogens therefrom, which serves to links two structures together.

The term "heteroaryl" used alone or as a suffix or prefix, refers to a heterocyclyl having aromatic character, wherein the radical of the heterocyclyl is located on a carbon of an aromatic ring of the heterocyclyl.

The term "heterocylcoalkyl" used alone or as a suffix or prefix, refers to a heterocyclyl that does not have aromatic character.

The term "heteroarylene" used alone or as a suffix or prefix, refers to a heterocyclylene having aromatic character.

The term "heterocycloalkylene" used alone or as a suffix or prefix, refers to a heterocyclylene that does not have aromatic character.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "substituted" used as a prefix refers to a structure, molecule or group, wherein one or more hydrogens are replaced with one or more $C_{1-12}$hydrocarbon groups, or one or more chemical groups containing one or more heteroatoms selected from N, O, S, F, Cl, Br, I, and P. Exemplary chemical groups containing one or more heteroatoms include heterocyclyl, —$NO_2$, —OR, —Cl, —Br, —I, —F, —$CF_3$, —C(=O)R, —C(=O)OH, —$NH_2$, —SH, —NHR, —$NR_2$, —SR, —$SO_3$H, —$SO_2$R, —S(=O)R, —CN, —OH, —C(=O)OR, —C(=O)$NR_2$, —NRC(=O)R, oxo (=O), imino (=NR), thio (=S), and oximino (=N—OR), wherein each "R" is a $C_{1-12}$hydrocarbyl. For example, substituted phenyl may refer to nitrophenyl, pyridylphenyl, methoxyphenyl, chlorophenyl, aminophenyl, etc., wherein the nitro, pyridyl, methoxy, chloro, and amino groups may replace any suitable hydrogen on the phenyl ring.

The term "substituted" used as a suffix of a first structure, molecule or group, followed by one or more names of chemical groups refers to a second structure, molecule or group, which is a result of replacing one or more hydrogens of the first structure, molecule or group with the one or more named chemical groups. For example, a "phenyl substituted by nitro" refers to nitrophenyl.

The term "optionally substituted" refers to both groups, structures, or molecules that are substituted and those that are not substituted.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3, 4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general formula —O—R, wherein —R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "aryloxy" used alone or as suffix or prefix, refers to radicals of the general formula —O—Ar, wherein —Ar is an aryl.

The term "heteroaryloxy" used alone or as suffix or prefix, refers to radicals of the general formula —O—Ar', wherein —Ar' is a heteroaryl.

The term "amine" or "amino" used alone or as a suffix or prefix, refers to radicals of the general formula —NRR', wherein R and R' are independently selected from hydrogen or a hydrocarbon radical.

"Acyl" used alone, as a prefix or suffix, means C(=O)—R, wherein —R is an optionally substituted hydrocarbyl, hydrogen, amino or alkoxy. Acyl groups include, for example, acetyl, propionyl, benzoyl, phenyl acetyl, carboethoxy, and dimethylcarbamoyl.

Halogen includes fluorine, chlorine, bromine and iodine.

"Halogenated," used as a prefix of a group, means one or more hydrogens on the group is replaced with one or more halogens.

"RT" or "rt" means room temperature.

A first ring group being "fused" with a second ring group means the first ring and the second ring share at least two atoms therebetween.

"Link," "linked," or "linking," unless otherwise specified, means covalently linked or bonded.

When a first group, structure, or atom is "directly connected" to a second group, structure or atom, at least one atom of the first group, structure or atom forms a chemical bond with at least one atom of the second group, structure or atom.

"Saturated carbon" means a carbon atom in a structure, molecule or group wherein all the bonds connected to this carbon atom are single bond. In other words, there is no double or triple bonds connected to this carbon atom and this carbon atom generally adopts an $sp^3$ atomic orbital hybridization.

"Unsaturated carbon" means a carbon atom in a structure, molecule or group wherein at least one bond connected to this carbon atom is not a single bond. In other words, there is at least one double or triple bond connected to this carbon atom and this carbon atom generally adopts a sp or $sp^2$ atomic orbital hybridization.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

SUMMARY OF THE INVENTION

This invention encompasses compounds in accord with formula I:

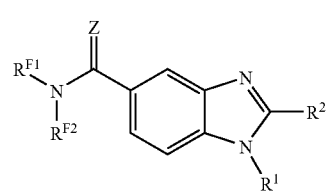

wherein $R^{F1}$ and $R^{F2}$ are independently $C_{1-6}$alkyl substituted by one or more groups selected from —F, —Cl, —Br, —NO$_2$, —CN, —OH, —CHO, —C(=O)—R' and —OR', wherein R' is a $C_{1-3}$alkyl;

Z is selected from O= and S=;

$R^1$ is selected from $C_{1-10}$alkyl, $C_{2-10}$alkenyl, $C_{2-10}$alkynyl, $R^3R^4N$—$C_{1-6}$alkyl, $R^3O$—$C_{1-6}$alkyl, $R^3C(=O)N(-R^4)$—$C_{1-6}$alkyl, $R^3R^4NS(=O)_2$—$C_{1-6}$alkyl, $R^3CS(=O)_2N(-R^4)$—$C_{1-6}$alkyl, $R^3R^4NC(=O)N(-R^5)$—$C_{1-6}$alkyl, $R^3R^4NS(=O)_2N(R^5)$—$C_{1-6}$alkyl, $C_{6-10}$aryl-$C_{1-6}$alkyl, $C_{6-10}$aryl-$C(=O)$—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-$C(=O)$—$C_{1-6}$alkyl, $R^3R^4N$—, $R^3O$—, $R^3C(=O)N(-R^4)$—, $R^3R^4NS(=O)_2$—, $R^3CS(=O)_2N(-R^4)$—, $R^3R^4NC(=O)N(-R^5)$—, $R^3R^4NS(=O)_2N(R^5)$—, $C_{6-10}$aryl, $C_{6-10}$aryl-$C(=O)$—, $C_{3-10}$cycloalkyl, $C_{4-8}$cycloalkenyl, $C_{3-6}$heterocyclyl and $C_{3-6}$heterocyclyl-$C(=O)$—; wherein said $C_{1-10}$alkyl, $C_{2-10}$alkenyl, $C_{2-10}$alkynyl, $C_{6-10}$aryl-$C_{1-6}$alkyl, $C_{6-10}$aryl-$C(=O)$—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-$C(=O)$—$C_{1-6}$alkyl, $C_{1-10}$hydrocarbylamino, $C_{6-10}$aryl, $C_{6-10}$aryl-$C(=O)$—, $C_{3-10}$cycloalkyl, $C_{4-8}$cycloalkenyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy and amino;

$R^2$ is selected from the group consisting of $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $R^3R^4N$—, $C_{3-5}$heteroaryl, $C_{6-10}$aryl and $C_{3-6}$heterocycloalkyl, wherein said $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $C_{3-5}$heteroaryl, $C_{6-10}$aryl or $C_{3-6}$heterocycloalkyl used in defining $R^2$ is optionally substituted by one or more groups selected from halogen, cyano, nitro, methoxy, ethoxy, methyl, ethyl, hydroxy, and $R^3R^4N$—; and $R^3$, $R^4$ and $R^5$ are independently selected from —H, $C_{1-6}$alkyl, $C_{2-6}$alkenyl, $C_{2-6}$alkynyl, and a divalent $C_{1-6}$ group that together with another divalent $C_{1-6}$ group selected from $R^3$, $R^4$ and $R^5$ forms a portion of a ring.

The invention also encompasses stereoisomers, enantiomers, diastereomers, racemates or mixtures thereof, in-vivo-hydrolysable precursors and pharmaceutically-acceptable salts of compounds of formula I, solvated or unsolvated forms of compounds of formula I, pharmaceutical compositions and formulations containing them, methods of using them to treat diseases and conditions either alone or in combination with other therapeutically-active compounds or substances, processes and intermediates used to prepare them, uses of them as medicaments, uses of them in the manufacture of medicaments and uses of them for diagnostic and analytic purposes.

DESCRIPTION OF PREFERRED EMBODIMENTS

In one aspect, the invention provides a compound of formula I, a pharmaceutically acceptable salt thereof, diastereomers, enantiomers, or mixtures thereof:

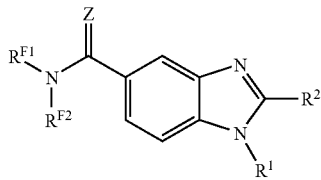

I wherein $R^{F1}$ and $R^{F2}$ are independently $C_{1-6}$alkyl substituted by one or more groups selected from —F, —Cl, —Br, —$NO_2$, —CN, —OH, —CHO, —C(=O)—R' and —OR', wherein R' is a $C_{1-3}$alkyl;

Z is selected from O= and S=;

$R^1$ is selected from $C_{1-10}$ alkyl, $C_{2-10}$alkenyl, $C_{2-10}$alkynyl, $R^3R^4N$—$C_{1-6}$alkyl, $R^3O$—$C_{1-6}$alkyl, $R^3C(=O)N(-R^4)$—$C_{1-6}$alkyl, $R^3R^4NS(=O)_2$—$C_{1-6}$alkyl, $R^3CS(=O)_2N(-R^4)$—$C_{1-6}$alkyl, $R^3R^4NC(=O)N(-R^5)$—$C_{1-6}$alkyl, $R^3R^4NS(=O)_2N(R^5)$—$C_{1-6}$alkyl, $C_{6-10}$aryl-$C_{1-6}$alkyl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $R^3R^4N$—, $R^3O$—, $R^3C(=O)N(-R^4)$—, $R^3R^4NS(=O)_2$—, $R^3CS(=O)_2N(-R^4)$—, $R^3R^4NC(=O)N(-R^5)$—, $R^3R^4NS(=O)_2N(R^5)$—, $C^{6-10}$aryl, $C_{6-10}$aryl-C(=O)—, $C_{3-10}$cycloalkyl, $C_{4-8}$cycloalkenyl, $C_{3-6}$heterocyclyl and $C_{3-6}$heterocyclyl-C(=O)—; wherein said $C_{1-10}$alkyl, $C_{2-10}$alkenyl, $C_{2-10}$alkynyl, $C_{6-10}$aryl-$C_{1-6}$alkyl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $C_{1-10}$hydrocarbylamino, $C_{6-10}$aryl, $C_{6-10}$aryl-C(=O)—, $C_{3-10}$cycloalkyl, $C_{4-8}$cycloalkenyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy and amino;

$R^2$ is selected from the group consisting of $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $R^3R^4N$—, $C_{3-5}$heteroaryl, $C_{6-10}$aryl and $C_{3-6}$heterocycloalkyl, wherein said $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $C_{3-5}$heteroaryl, $C_{6-10}$aryl or $C_{3-6}$heterocycloalkyl used in defining $R^2$ is optionally substituted by one or more groups selected from halogen, cyano, nitro, methoxy, ethoxy, methyl, ethyl, hydroxy, and $R^3R^4N$—; and $R^3$, $R^4$ and $R^5$ are independently selected from —H, $C_{1-6}$alkyl, $C_{2-6}$alkenyl, $C_{2-6}$alkynyl, and a divalent $C_{1-6}$ group that together with another divalent $C_{1-6}$ group selected from $R^3$, $R^4$ and $R^5$ forms a portion of a ring.

Particularly, the compounds of the present invention are those of formula I, wherein $R^{F1}$ and $R^{F2}$ are independently selected from —$CF_3$, —$CH_2CF_3$, —$CH_2CHF_2$, —$CHFCF_3$, —$CHFCHF_2$, —$CHFCH_2F$, —$CF_2CF_3$, —$CF_2CH_3$, —$CF_2CH_2F$, —$CF_2CHF_2$, —$CF_3$, —$CH_2CCl_3$, —$CH_2CHCl_2$, —$CH_2CBr_3$, —$CH_2CHBr_2$, —$CH_2NO_2$, —$CH_2CH_2NO_2$, —$CH_2CN$, —$CH_2CH_2CN$, and —$CH_2CH_2OCH_3$;

Z is O=;

$R^1$ is selected from $C_{1-6}$alkyl, $C_{2-6}$alkenyl, $C_{2-6}$alkynyl, $R^3R^4N$—$C_{1-4}$alkyl, $R^3O$—$C_{1-4}$alkyl, $R^3C(=O)N(-R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, $R^3R^4N$—, $R^3O$—, $R^3R^4NS(=O)_2$—, $C_{6-10}$aryl, $C_{6-10}$aryl-C(=O)—, $C_{3-10}$cycloalkyl, $C_{4-6}$cycloalkenyl, $C_{3-6}$heterocyclyl and $C_{3-6}$heterocyclyl-C(=O)—; wherein said $C_{1-6}$alkyl, $C_{2-6}$alkenyl, $C_{2-6}$alkynyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, $C_{6-10}$aryl, $C_{6-10}$aryl-C(=O)—, $C_{3-10}$cycloalkyl, $C_{4-6}$cycloalkenyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy, and $R^3R^4N$—;

$R^2$ is selected from the group consisting of $C_{1-6}$alkyl, $C_{2-6}$alkenyl, $C_{3-6}$cycloalkyl, $C_{3-6}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkenyl, $C_{3-5}$heteroaryl, $R^3R^4N$—, phenyl and $C_{3-6}$heterocycloalkyl, wherein said $C_{1-6}$alkyl, $C_{2-6}$alkenyl, $C_{3-6}$cycloalkyl, $C_{3-6}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkenyl, $C_{3-5}$heteroaryl, phenyl or $C_{3-6}$heterocycloalkyl used in defining $R^2$ is optionally substituted by one or more groups selected from halogen, cyano, nitro, methoxy, ethoxy, methyl, ethyl, hydroxy, and $R^3R^4N$—; and $R^3$ and $R^4$ are independently selected from —H, $C_{1-6}$alkyl and $C_{2-6}$alkenyl.

More particularly, the compounds of the present invention are those of formula I, wherein $R^{F1}$ and $R^{F2}$ are independently selected from —$CF_3$, —$CH_2CF_3$, —$CH_2CHF_2$, —$CHFCF_3$, —$CHFCHF_2$, —$CHFCH_2F$, —$CF_2CF_3$, —$CF_2CH_3$, —$CF_2CH_2F$, —$CF_2CHF_2$, and —$CF_3$;

Z is O=;

$R^1$ is selected from $C_{1-6}$alkyl, $C_{2-6}$alkenyl, $R^3R^4N$—, $R^3R^4N$—$C_{1-4}$alkyl, $R^3O$—$C_{1-4}$alkyl, $R^3C(=O)N(-R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, phenyl, $C_{3-10}$cycloalkyl, $C_{3-6}$heterocyclyl and $C_{3-6}$heterocyclyl-C(=O)—; wherein said $C_{1-6}$alkyl, $C_{2-6}$alkenyl, $R^3R^4N$—$C_{1-4}$alkyl, $R^3O$—$C_{1-4}$alkyl, $R^3C(=O)N(-R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, phenyl, $C_{3-10}$cycloalkyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy and $R^3R^4N$—;

$R^2$ is selected from the group consisting of $C_{1-6}$alkyl, $C_{3-6}$cycloalkyl, $R^3R^4N$—, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl wherein said $C_{1-6}$alkyl, $C_{3-6}$cycloalkyl, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl used in defining $R^2$ is optionally substituted by one or more groups selected from halogen, cyano, nitro, methoxy, ethoxy, methyl, ethyl, hydroxy and $R^3R^4N$—; and $R^3$ and $R^4$ are independently selected from —H, $C_{3-6}$alkyl and $C_{2-6}$alkenyl.

Most particularly, the compounds of the present invention are those of formula I, wherein $R^{F1}$ and $R^{F2}$ are —$CH_2CF_3$;

Z is O=;

$R^1$ is selected from cyclohexylmethyl, cyclopentylmethyl, cyclobutylmethyl, cyclopropylmethyl, ethyl, propyl, adamantyl, adamantylmethyl, allyl, isopentyl, benzyl, methoxyethyl, tetrahydropyranylmethyl, tetrahydrofuranylmethyl, cyclohexyloxy, cyclohexylamino, dimethylaminoethyl, 4-pyridylmethyl, 2-pyridylmethyl, 1-pyrrolylethyl, 1-morpholinoethyl, 4,4-difluorocyclohexylmethyl, cyclohexylmethyl, 2-pyrrolidylmehtyl, N-methyl-2-pyrrolidylmethyl, 2-piperidylmethyl, N-methyl-2-piperidylmethyl, 3-thienylmethyl, (2-nitrothiophene-5-yl)-methyl, (1-methyl-1H-imidazole-2-yl)methyl, (5-(acetoxymethyl)-2-furyl)methyl), (2,3-dihydro-1H-isoindole-1-yl)methyl, and 5-(2-methylthiazolyl); and $R^2$ is selected from t-butyl, n-butyl, 2-methyl-2-butyl, cyclohexyl, cyclohexylmethyl, n-pentyl, isopentyl, trifluoromethyl, 1,1,-difluoroethyl, N-piperidyl, dimethylamino, phenyl, pyridyl, tetrahydrofuranyl, tetrahydropyranyl, 2-methoxy-2-propyl and N-morpholinyl.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have now found that the compounds of the invention have activity as pharmaceuticals, in particular as modulators or ligands such as agonists, partial agonists, inverse agonist or antagonists of CB1 receptors. More particularly, the compounds of the invention exhibit selective activity as agonist of the CB1 receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of CB1 receptors is present or implicated. Furthermore, the compounds of the invention may be used to treat cancer, multiple sclerosis, Parkinson's disease, Huntington's chorea, Alzheimer's disease, anxiety disorders, gastrointestinal disorders and cardiovascular disorders.

Compounds of the invention are useful as immunomodulators, especially for autoimmune diseases, such as arthritis, for skin grafts, organ transplants and similar surgical needs, for collagen diseases, various allergies, for use as antitumour agents and anti viral agents.

Compounds of the invention are useful in disease states where degeneration or dysfunction of cannabinoid receptors is present or implicated in that paradigm. This may involve the use of isotopically labelled versions of the compounds of the invention in diagnostic techniques and imaging applications such as positron emission tomography (PET).

Compounds of the invention are useful for the treatment of diarrhoea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following myocardial infarction, spinal injury and drug addiction, including the treatment of alcohol, nicotine, opioid and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Also within the scope of the invention is the use of any of the compounds according to the formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be contrued accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (per cent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In a further aspect, the present invention provides a method of preparing the compounds of the present invention.

In one embodiment, the invention provides a process for preparing a compound of formula I,

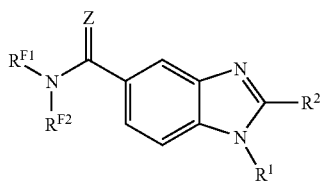

I comprising the step of reacting a compound of formula II,

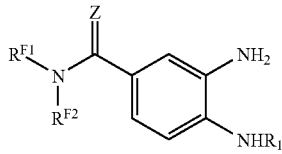

II with a compound of $R^2C(=O)-X$ to form the compound of formula I, wherein $R^{F1}$ and $R^{F2}$ are independently selected from $-CF_3$, $-CH_2CF_3$, $-CH_2CHF_2$, $-CHFCF_3$, $-CHFCHF_2$, $-CHFCH_2F$, $-CF_2CF_3$, $-CF_2CH_3$, $-CF_2CH_2F$, $-CF_2CHF_2$, and $-CF_3$;

Z is selected from O= and S=;

X is selected from $-Cl$, $-Br$, $-I$, $-OH$, $-OCH_3$, and $-OCH_2CH_3$;

$R^1$ is selected from $C_{1-6}$alkyl, $C_{2-6}$alkenyl, $R^3R^4N-C_{1-4}$alkyl, $R^3O-C_{1-4}$alkyl, $R^3C(=O)N(-R^4)-C_{1-4}$alkyl, phenyl-$C_{1-4}$alkyl, phenyl-$C(=O)-C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$ alkyl, $C_{3-6}$heterocyclyl-$C(=O)-C_{1-4}$alkyl, phenyl, $C_{3-10}$cycloalkyl, $C_{3-6}$heterocyclyl and $C_{3-6}$heterocyclyl-$C(=O)-$; wherein said $C_{1-6}$alkyl, $C_{2-6}$alkenyl, $R^3R^4N-C_{1-4}$alkyl, $R^3O-C_{1-4}$alkyl, $R^3C(=O)N(-R^4)-C_{1-4}$alkyl, phenyl-$C_{1-4}$alkyl, phenyl-$C(=O)-C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$ alkyl, $C_{3-6}$heterocyclyl-$C(=O)-C_{1-4}$alkyl, phenyl, $C_{3-10}$cycloalkyl, $C_{3-6}$heterocyclyl or $C_{3-6}$heterocyclyl-$C(=O)-$ used in defining $R^1$ is optionally substituted by one or more groups selected from halogen, cyano, nitro, methoxy, ethoxy, methyl, ethyl, hydroxy, and $R^3R^4N-$;

$R^2$ is selected from the group consisting of $C_{1-6}$alkyl, $C_{3-6}$cycloalkyl, $R^3R^4N-$, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl wherein said $C_{1-6}$alkyl, $C_{3-6}$cycloalkyl, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl used in defining $R^2$ is optionally substituted by one or more groups selected from halogen, cyano, nitro, methoxy, ethoxy, methyl, ethyl, hydroxy and $R^3R^4N-$; and $R^3$ and $R^4$ are independently selected from $-H$, $C_{1-6}$alkyl and $C_{2-6}$alkenyl.

Particularly, the present invention provides a method of preparing a compound of formula I, wherein $R^{F1}$ and $R^{F2}$ are $-CH_2CF_3$; Z is O=; X is Cl or Br;

$R^1$ is selected from cyclohexylmethyl, cyclopentylmethyl, cyclobutylmethyl, cyclopropylmethyl, ethyl, propyl, adamantyl, adamantylmethyl, allyl, isopentyl, benzyl, methoxyethyl, tetrahydropyranylmethyl, tetrahydrofuranylmethyl, cyclohexyloxy, cyclohexylamino, dimethylaminoethyl, 4-pyridylmethyl, 2-pyridylmethyl, 1-pyrrolylethyl, 1-morpholinoethyl, 4,4-difluorocyclohexylmethyl, cyclohexylmethyl, 2-pyrrolidylmehtyl, N-methyl-2-pyrrolidylmethyl, 2-piperidylmethyl, N-methyl-2-piperidylmethyl, 3-thienylmethyl, (2-nitrothiophene-5-yl)-methyl, (1-methyl-1H-imidazole-2-yl)methyl, (5-(acetoxymethyl)-2-furyl)methyl), (2,3-dihydro-1H-isoindole-1-yl)methyl, and 5-(2-methylthiazolyl); and $R^2$ is selected from t-butyl, n-butyl, 2-methyl-2-butyl, cyclohexyl, cyclohexylmethyl, n-pentyl, isopentyl, trifluoromethyl, 1,1-difluoroethyl, N-piperidyl, dimethylamino, phenyl, pyridyl, tetrahydrofuranyl, tetrahydropyranyl, 2-methoxy-2-propyl and N-morpholinyl.

Compounds of the present invention may be prepared according to the synthetic routes as depicted in Scheme 1 using one or more methods disclosed above.

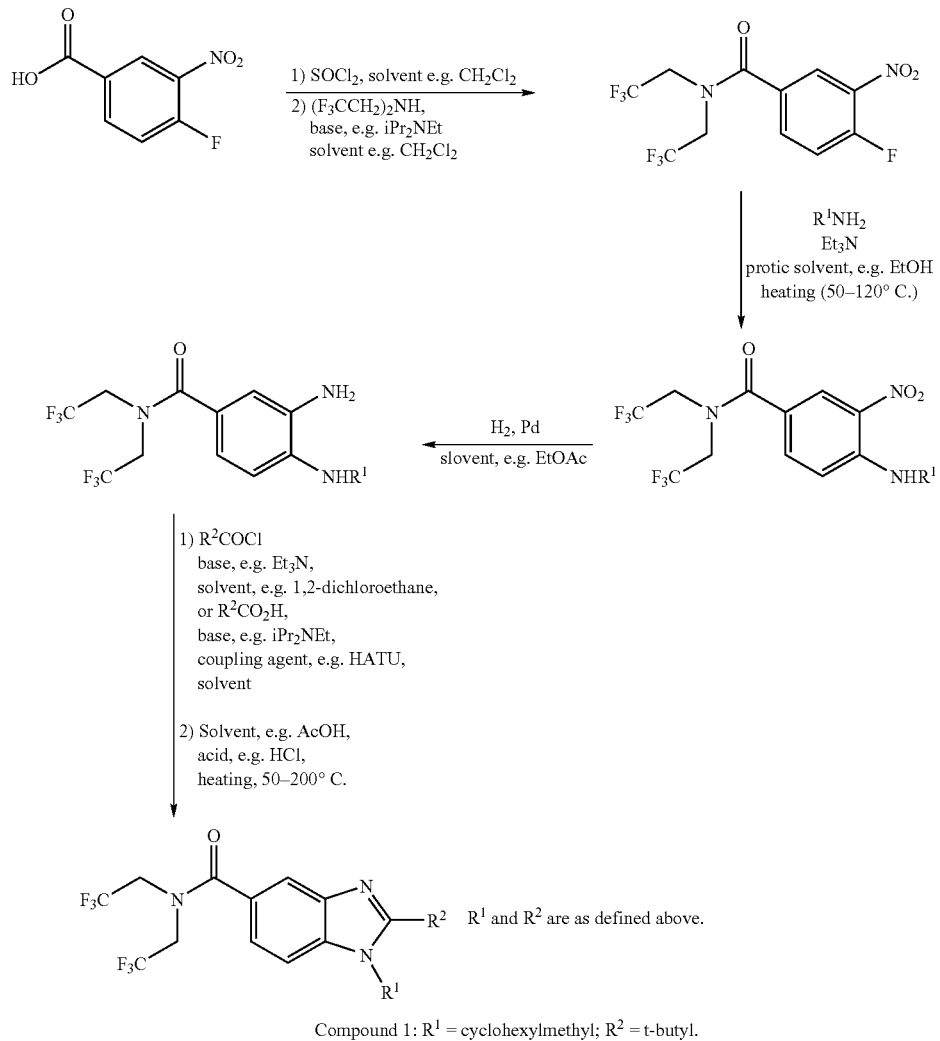

Compound 1: $R^1$ = cyclohexylmethyl; $R^2$ = t-butyl.

Biological Evaluation $hCB_1$ and $hCB_2$ Receptor Binding

Human $CB_1$ receptor from Receptor Biology (hCB1) or human $CB_2$ receptor from BioSignal (hCB2) membranes are thawed at 37° C., passed 3 times through a 25-gauge blunt-end needle, diluted in the cannabinoid binding buffer (50 mM Tris, 2.5 mM EDTA, 5 mM $MgCl_2$, and 0.5 mg/mL BSA fatty acid free, pH 7.4) and aliquots containing the appropriate amount of protein are distributed in 96-well plates. The $IC_{50}$ of the compounds of the invention at $hCB_1$ and $hCB_2$ are evaluated from 10-point dose-response curves done with $^3$H-CP55,940 at 20000 to 25000 dpm per well (0.17-0.21 nM) in a final volume of 300 μl. The total and non-specific binding are determined in the absence and presence of 0.2 μM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM $MgCl_2$, 0.5 mg BSA pH 7.0). The filters are dried for 1 hour at 55° C. The radioactivity (cpm) is counted in a TopCount (Packard) after adding 65 μl/well of MS-20 scintillation liquid.

$hCB_1$ and $hCB_2$ GTPγS Binding

Human $CB_1$ receptor from Receptor Biology (hCB1) or human $CB_2$ receptor membranes (BioSignal) are thawed at 37° C., passed 3 times through a 25-gauge blunt-end needle and diluted in the GTPγS binding buffer (50 mM Hepes, 20 mM NaOH, 100 mM NaCl, 1 mM EDTA, 5 mM $MgCl_2$, pH 7.4, 0.1% BSA). The $EC_{50}$ and $E_{max}$ of the compounds of the invention are evaluated from 10-point dose-response curves done in 300 μl with the appropriate amount of membrane protein and 100000-130000 dpm of GTPg$^{35}$S per well (0.11-0.14 nM). The basal and maximal stimulated binding is determined in absence and presence of 1 μM ($hCB_2$) or 10 μM ($hCB_1$) Win 55,212-2 respectively. The membranes are pre-incubated for 5 minutes with 56.25 μM (hCB2) or 112.5 μM ($hCB_1$) GDP prior to distribution in plates (15 μM ($hCB_2$) or 30 μM ($hCB_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM $MgCl_2$, 50 mM NaCl, pH 7.0). The filters are dried for 1 hour at 55° C. The radioactivity (cpm) is counted in a TopCount (Packard) after adding 65 μl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki=IC_{50}/(1+[\text{rad}]/Kd),$$

Wherein $IC_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Using above-mentioned assays, the Ki towards human $CB_1$ receptors for compound 1 (scheme 1) of the invention is measured to be about 34 nM. The Ki towards human $CB_2$ receptors for compound 1 (scheme 1) of the invention is measured to be about 33 nM.

EXAMPLES

The invention will further be described in more detail by the following Examples which describe methods whereby compounds of the present invention may be prepared, purified, analyzed and biologically tested, and which are not to be construed as limiting the invention.

Example 1

2-tert-Butyl-1-(cyclohexylmethyl)-N,N-bis(2,2,2-trifluoroethyl)1H-benzimidazole-5-carboxamide

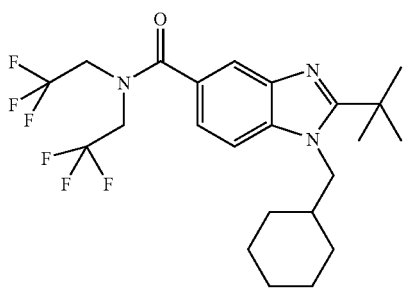

Step A. 2-tert-Butyl-1-(cyclohexylmethyl)-N,N-bis (2,2,2-trifluoroethyl)-1H-benzimidazole-5-carboxamide

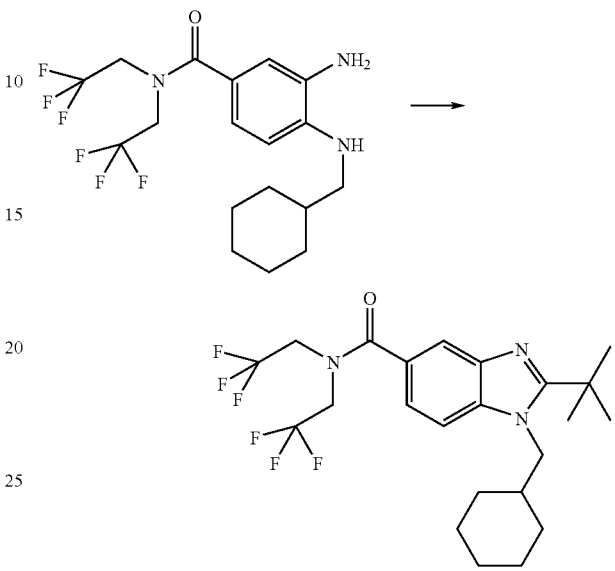

3-Amino-4-[(cyclohexylmethyl)amino]-N,N-bis(2,2,2-trifluoroethyl)benzamide (102 mg, 0.248 mmol) (for preparation, see the following steps B, C and D) was dissolved in 3 mL of DCE containing TEA (0.050 mL, 0.372 mmol). Trimethylacetyl chloride (0.035 mL, 0.272 mmol) was added dropwise and the solution stirred at RT for 1 h. Glacial AcOH (1 mL) and a few drops of concentrated HCl were added and the solution stirred at 75° C. for 24 h. The resulting mixture was concentrated. The residue was dissolved in EtOAc and washed with 2M NaOH, brine and dried over anhydrous $MgSO_4$. The solvent was evaporated. The product was purified by a reversed-phase HPLC using 20-80% $CH_3CN/H_2O$ and then lyophilized affording the title product as the corresponding TFA salt. Yield: 51 mg (35%). $^1$H NMR (400 MHz, $CD_3OD$) δ 1.23 (m, 9H), 1.66 (m, 8H), 1.75 (m, 2H), 2.11 (m, 1H), 4.35 (brs, 4H), 4.47 (d, J=7.62 Hz, 2H), 7.61 (dd, J=1.56, 8.79 Hz, 1H), 7.79 (s, 1H), 8.01 (d, J=8.59 Hz, 1H); MS (ESI) (M+H)$^+$ 478.2; Anal. Calcd for $C_{23}H_{29}N_3OF_6$+1.2 TFA+0.8 $H_2O$: C, 48.52; H, 5.10; N, 6.68. Found: C, 48.62; H, 5.19; N, 6.56.

Step B. 4-Fluoro-3-nitro-N,N-bis(2,2,2-trifluoroethyl)benzamide

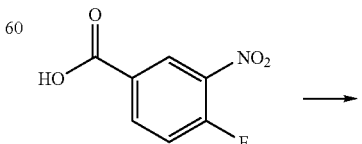

-continued

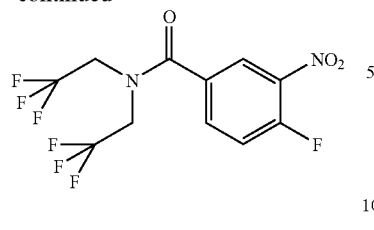

4-Fluoro-3-nitrobenzoic acid (2.50 g, 13.5 mmol) was refluxed in a 2:1 mixture of $CH_2Cl_2/SOCl_2$ (150 mL) for 5 h. The solvent was concentrated and the residue was dissolved in $CH_2Cl_2$ (50 mL). Another $CH_2Cl_2$ solution (50 mL) of diisopropylethylamine (DIPEA) (3.50 mL, 20.3 mmol) and bis(2,2,2-trifluoroethyl)amine (4.90 g, 27.0 mmol) was then added dropwise to the cold stirring solution (0° C.) of the acid chloride. The solution was stirred at rt overnight. The solution was then washed with 5% $KHSO_4$ solution, saturated $NaHCO_3$ solution, brine and dried over anhydrous $MgSO_4$. The crude product was purified by flash chromatography using 3:1/hexanes:EtOAc to afford the title product. Yield: 3.08 g (66%). $^1H$ NMR (400 MHz, $CDCl_3$) δ 4.17 (brs, 4H), 7.40 (t, J=8.59 Hz, 1H), 7.66 (m, 2H), 8.10 (d, J=6.84 Hz, 1H).

Step C. 4-[(Cyclohexylmethyl)amino]-3-nitro-N,N-bis(2,2,2-trifluoroethyl)benzamide

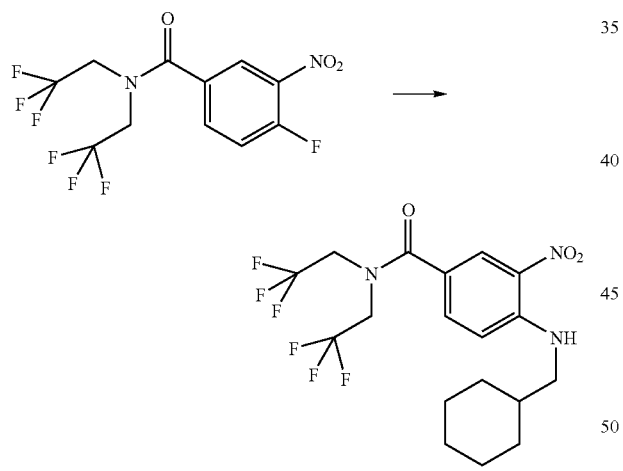

4-Fluoro-3-nitro-N,N-bis(2,2,2-trifluoroethyl)benzamide (107 mg, 0.307 mmol) and cyclohexylmethylamine (0.050 mL, 0.368 mmol) were stirred in 3 mL of EtOH containing TEA (0.065 mL, 0.460 mmol) at 75° C. for 3 h. The mixture was concentrated. The residue was re-dissolved in EtOAc and washed with 5% $KHSO_4$ solution, saturated $NaHCO_3$ solution, brine and dried over anhydrous $MgSO_4$. The title product was purified by flash chromatography using 9:1/hexanes:EtOAc. Yield: 113 mg (83%). $^1H$ NMR (400 MHz, $CDCl_3$) δ 1.05 (m, 2H), 1.24 (m, 4H), 1.69 (m, 2H), 1.75 (m, 2H), 1.83 (m, 1H), 3.17 (t, J=6.64 Hz, 2H), 4.23 (q, J=8.53 Hz, 4H), 6.91 (d, J=8.98 Hz, 1H), 7.51 (d, J=8.89 Hz, 1H), 8.28 (s, 1H), 8.39 (s, 1H).

Step D. 3-Amino-4-[(cyclohexylmethyl)amino]-N,N-bis(2,2,2-trifluoroethyl)benzamide

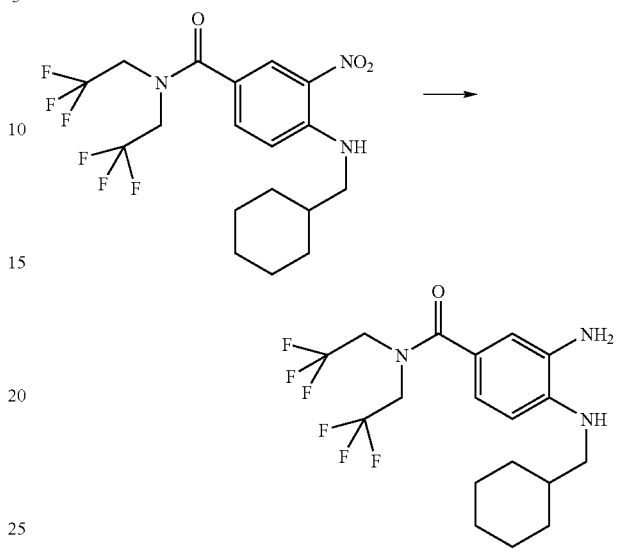

4-[(Cyclohexylmethyl)amino]-3-nitro-N,N-bis(2,2,2-trifluoroethyl)benzamide (110 mg, 0.249 mmol) was dissolved in 15 mL of EtOAc containing a catalytic amount of 10% Pd/C. The solution was shaken in a Parr hydrogenation apparatus under $H_2$ atmosphere (40 psi) overnight at rt. The solution was filtered through Celite and the solvent concentrated. The title product was used directly for the next step without further purification. Yield: 102 mg (99%). MS (ESI) $(M+H)^+$ 411.9.

The invention claimed is:

1. A compound of formula I or a pharmaceutically acceptable salt thereof:

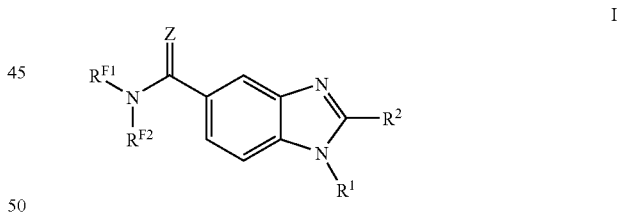

wherein $R^{F1}$ and $R^{F2}$ are independently $C_{1-6}$alkyl substituted by one or more groups selected from —F, —Cl, —Br, —$NO_2$, —CN, —OH, —CHO, —C(=O)—R' and —OR', wherein R' is a $C_{1-3}$alkyl;

Z is selected from O= and S=;

$R^1$ is selected from $C_{1-10}$alkyl, $C_{2-10}$alkenyl, $C_{2-10}$alkynyl, $R^3R^4N$—$C_{1-6}$alkyl, $R^3O$—$C_{1-6}$alkyl, $R^3C(=O)N(-R^4)$—$C_{1-6}$alkyl, $R^3R^4NS(=O)_2$—$C_{1-6}$alkyl, $R^3CS(=O)_2N(-R^4)$—$C_{1-6}$alkyl, $R^3R^4NC(=O)N(-R^5)$—$C_{1-6}$alkyl, $R^3R^4NS(=O)_2N(R^5)$—$C_{1-6}$alkyl, $C_{6-10}$aryl-$C_{1-6}$alkyl, $C_{6-10}$aryl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $R^3R^4N$—, $R^3O$—, $R^3C(=O)N(-R^4)$—, $R^3R^4NS(=O)_2$—, $R^3CS(=O)_2N(-R^4)$—, $R^3R^4NC(=O)N(-R^5)-$, $R^3R^4NS(=O)_2N(R^5)-$, $C_{6-10}$aryl, $C_{6-10}$aryl-C(=O)—, $C_{3-10}$cycloalkyl, $C_{4-8}$cycloalkenyl, $C_{3-6}$heterocyclyl and $C_{3-6}$heterocyclyl-C(=O)—; wherein said $C_{1-10}$alkyl, $C_{2-10}$alkenyl, $C_{2-10}$alkynyl, $C_{6-10}$aryl-$C_{1-6}$alkyl, $C_{6-10}$aryl-C(=O)— $C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $C_{1-10}$hydrocarbylamino, $C_{6-10}$aryl, $C_{6-10}$aryl-C(=O)—, $C_{3-10}$cycloalkyl, $C_{4-8}$cycloalkenyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy, and $R^3R^4N$—;

$R^2$ is selected from the group consisting of $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $R^3R^4N$—, $C_{3-5}$heteroaryl, $C_{6-10}$aryl and $C_{3-6}$heterocycloalkyl, wherein said $C_{1-10}$alkyl, $C_{2-10}$alkenyl, $C_{2-10}$alkynyl, $C_{3-10}$cycloalkyl, $C_{3-10}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl, $C_{3-5}$heteroaryl, $C_{6-10}$aryl or $C_{3-6}$heterocycloalkyl used in defining $R^2$ is optionally substituted by one or more groups selected from halogen, cyano, nitro, methoxy, ethoxy, methyl, ethyl, hydroxy and $R^3R^4N$—; and $R^3$ and $R^4$ and are independently selected from —H, $C_{1-6}$alkyl, $C_{2-6}$alkenyl, and $C_{2-6}$alkynyl.

2. A compound as claimed in claim 1, wherein
$R^{F1}$ and $R^{F2}$ are independently selected from —$CF_3$, —$CH_2CF_3$, —$CH_2CHF_2$, —$CHFCF_3$, —$CHFCHF_2$, —$CHFCH_2F$, —$CF_2CF_3$, —$CF_2CH_3$, —$CF_2CH_2F$, —$CF_2CHF_2$, —$CF_3$, —$CH_2CCl_3$, —$CH_2CHCl_2$, —$CH_2CBr_3$, —$CH_2CHBr_2$, —$CH_2NO_2$, —$CH_2CH_2NO_2$, —$CH_2CN$, —$CH_2CH_2CN$, and —$CH_2CH_2OCH_3$;

Z is O=;

$R^1$ is selected from $C_{1-6}$alkyl, $C_{2-6}$alkenyl, $C_{2-6}$alkynyl, $R^3R^4N$—$C_{1-4}$alkyl, $R^3O$—$C_{1-4}$alkyl, $R^3C(=O)N(—R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, $R^3R^4N$—, $R^3O$—, $R^3R^4NS(=O)_2$—, $C_{6-10}$aryl, $C_{6-10}$aryl-C(=O)—, $C_{3-10}$cycloalkyl, $C_{4-6}$cycloalkenyl, $C_{3-6}$heterocyclyl and $C_{3-6}$heterocyclyl-C(=O)—; wherein said $C_{1-6}$alkyl, $C_{2-6}$alkenyl, $C_{2-6}$alkynyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, $C_{6-10}$aryl, $C_{6-10}$aryl-C(=O)—, $C_{3-10}$cycloalkyl, $C_{4-6}$cycloalkenyl, $C_{3-6}$heterocyclyl or $C_{3-6}$heterocyclyl-C(=O)—used in defining $R^1$ is optionally substituted by one or more groups selected from halogen, cyano, nitro, methoxy, ethoxy, methyl, ethyl, hydroxy and $R^3R^4N$—;

$R^2$ is selected from the group consisting of $C_{1-6}$alkyl, $C_{2-6}$alkenyl, $C_{3-10}$cycloalkyl, $C_{3-10}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkenyl, $C_{3-5}$heteroaryl, $R^3R^4N$—, phenyl and $C_{3-6}$heterocycloalkyl, wherein said $C_{1-6}$alkyl, $C_{2-6}$alkenyl, $C_{3-10}$cycloalkyl, $C_{3-10}$cycloalkyl-$C_{1-4}$alkyl, $C_{4-6}$cycloalkenyl-$C_{1-4}$alkyl, $C_{3-6}$heterocycloalkyl-$C_{1-4}$alkyl, $C_{4-6}$cycloalkyl, $C_{3-5}$heteroaryl, phenyl or $C_{3-6}$heterocycloalkyl used in defining $R^2$ is optionally substituted by one or more groups selected from halogen, cyano, nitro, methoxy, ethoxy, methyl, ethyl, hydroxy and $R^3R^4N$—; and $R^3$ and $R^4$ are independently selected from —H, $C_{1-6}$alkyl and $C_{2-6}$alkenyl.

3. A compound as claimed claim 1, wherein
$R^{F1}$ and $R^{F2}$ are independently selected from —$CF_3$, —$CH_2CF_3$, —$CH_2CHF_2$, —$CHFCF_3$, —$CHFCHF_2$, —$CHFCH_2F$, —$CF_2CF_3$, —$CF_2CH_3$, —$CF_2CH_2F$, —$CF_2CHF_2$, and —$CF_3$;

Z is O=;

$R^1$ is selected from $C_{1-6}$alkyl, $C_{2-6}$alkenyl, $R^3R^4N$—, $R^3R^4N$—$C_{1-4}$alkyl, $R^3O$—$C_{1-4}$alkyl, $R^3C(=O)N(—R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, phenyl, $C_{3-10}$cycloalkyl, $C_{3-6}$heterocyclyl and $C_{3-6}$heterocyclyl-C(=O)—; wherein said $C_{1-6}$alkyl, $C_{2-6}$alkenyl, $R^3R^4N$—$C_{1-4}$alkyl, $R^3O$—$C_{1-4}$alkyl, $R^3C(=O)N(—R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocyclyl-C(=O)—$C_{1-4}$alkyl, phenyl, $C_{3-10}$cycloalkyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy and $R^3R^4N$—;

$R^2$ is selected from the group consisting of $C_{1-6}$alkyl, $C_{3-10}$cycloalkyl, $R^3R^4N$—, $C_{3-10}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl wherein said $C_{1-6}$alkyl, $C_{3-10}$cycloalkyl, $C_{3-10}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl used in defining $R^2$ is optionally substituted by one or more groups selected from halogen, cyano, nitro, methoxy, ethoxy, methyl, ethyl, hydroxy and $R^3R^4N$—; and $R^3$ and $R^4$ are independently selected from —H, $C_{1-6}$alkyl and $C_{2-6}$alkenyl.

4. A compound as claimed in claim 1, wherein
$R^{F1}$ and $R^{F2}$ are —$CH_2CF_3$;

Z is O=;

$R^1$ is selected from cyclohexylmethyl, cyclopentylmethyl, cyclobutylmethyl, cyclopropylmethyl, ethyl, propyl, adamantyl, adamantylmethyl, allyl, isopentyl, benzyl, methoxyethyl, tetrahydropyranylmethyl, tetrahydrofuranylmethyl, cyclohexyloxy, cyclohexylamino, dimethylaminoethyl, 4-pyridylmethyl, 2-pyridylmethyl, 1-pyrrolylethyl, 1-morpholinoethyl, 4,4-difluorocyclohexylmethyl, cyclohexylmethyl, 2-pyrrolidylmethyl, N-methyl-2-pyrrolidylmethyl, 2-piperidylmethyl, N-methyl-2-piperidylmethyl, 3-thienylmethyl, (2-nitrothiophene-5-yl)-methyl, (1-methyl-1H-imidazole-2-yl)methyl, (5-(acetoxymethyl)-2-furyl)methyl), (2,3-dihydro-1H-isoindole-1-yl)methyl, and 5-(2-methylthiazolyl); and $R^2$ is selected from t-butyl, n-butyl, 2-methyl-2-butyl, cyclohexyl, cyclohexylmethyl, n-pentyl, isopentyl, trifluoromethyl, 1,1-difluoroethyl, N-piperidyl, dimethylamino, phenyl, pyridyl, tetrahydrofuranyl, tetrahydropyranyl, 2-methoxy-2-propyl, and N-morpholinyl.

5. A compound selected from 2-tert-Butyl-1-(cyclohexylmethyl)-N,N-bis(2,2,2-trifluoroethyl)-1H-benzimidazole-5-carboxamide and pharmaceutically acceptable salts thereof.

6. A pharmaceutical composition comprising a compound according to claim 1 and a pharmaceutically acceptable carrier.

7. A method for treating pain in a warm-blooded animal, comprising the step of administering to said animal in need of such therapy a therapeutically effective amount of a compound according to claim 1.

8. A method for preparing a compound of formula I,

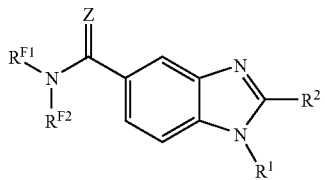

comprising the step of reacting a compound of formula II,

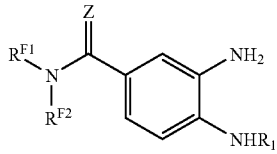

with a compound of $R^2C(=O)$—X to form the compound of formula I,
wherein
$R^{F1}$ and $R^{F2}$ are independently selected from —$CF_3$, —$CH_2CF_3$, —$CH_2CHF_2$, —$CHFCF_3$, —$CHFCHF_2$, —$CHFCH_2F$, —$CF_2CF_3$, —$CF_2CH_3$, —$CF_2CH_2F$, —$CF_2CHF_2$, and —$CF_3$;
Z is selected from O= and S=;
X is selected from —Cl, —Br, —I, —OH, —$OCH_3$, and —$OCH_2CH_3$;
$R^1$ is selected from $C_{1-6}$alkyl, $C_{2-6}$alkenyl, $R^3R^4N$—$C_{1-4}$alkyl, $R^3O$—$C_{1-4}$alkyl, $R^3C(=O)N(-R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocycly-C(=O)—$C_{1-4}$alkyl, phenyl, $C_{3-10}$cycloalkyl, $C_{3-6}$heterocyclyl and $C_{3-6}$heterocyclyl-C(=O)—; wherein said $C_{1-6}$alkyl, $C_{2-6}$alkenyl, $R^3R^4N$—$C_{1-4}$alkyl, $R^3O$—$C_{1-4}$alkyl, $R^3C(=O)N(-R^4)$—$C_{1-4}$alkyl, phenyl-$C_{1-4}$alkyl, phenyl-C(=O)—$C_{1-4}$alkyl, $C_{3-10}$cycloalkyl-$C_{1-4}$alkyl, $C_{4-6}$cycloalkenyl-$C_{1-4}$alkyl, $C_{3-6}$heterocyclyl-$C_{1-4}$alkyl, $C_{3-6}$heterocycly-C(=O)—$C_{1-4}$alkyl, phenyl, $C_{3-10}$cycloalkyl, $C_{3-6}$heterocyclyl or $C_{3-6}$heterocyclyl-C(=O)— used in defining $R^1$ is optionally substituted by one or more groups selected from halogen, cyano, nitro, methoxy, ethoxy, methyl, ethyl, hydroxy, and $R^3R^4N$—;
$R^2$ is selected from the group consisting of $C_{1-6}$alkyl, $C_{3-6}$cycloalkyl, $R^3R^4N$—, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl wherein said $C_{1-6}$alkyl, $C_{3-6}$cycloalkyl, $C_{3-6}$cycloalkyl-$C_{1-4}$alkyl, $C_{3-6}$heterocycloalkyl-$C_{1-4}$alkyl, $C_{3-6}$heterocycloalkyl, $C_{3-5}$heteroaryl, and phenyl used in defining $R^2$ is optionally substituted by one or more groups selected from halogen, cyano, nitro, methoxy, ethoxy, methyl, ethyl, hydroxy and amino; and
$R^3$ and $R^4$ are independently selected from —H, $C_{1-6}$alkyl and $C_{2-6}$alkenyl.

9. A pharmaceutical composition comprising a compound according to claim 2 and a pharmaceutically acceptable carrier.

10. A pharmaceutical composition comprising a compound according to claim 4 and a pharmaceutically acceptable carrier.

11. A pharmaceutical composition comprising a compound according to claim 5 and a pharmaceutically acceptable carrier.

12. A method for treating pain in a warm-blooded animal, comprising the step of administering to said animal in need of such therapy a therapeutically effective amount of a compound according to claim 2.

13. A method for treating pain in a warm-blooded animal, comprising the step of administering to said animal in need of such therapy a therapeutically effective amount of a compound according to claim 4.

14. A method for treating pain in a warm-blooded animal, comprising the step of administering to said animal in need of such therapy a therapeutically effective amount of a compound according to claim 5.

* * * * *